United States Patent
Koren

(10) Patent No.: US 10,130,547 B2
(45) Date of Patent: Nov. 20, 2018

(54) EXOSKELETON DEVICE WITH SITTING SUPPORT AND METHOD OF OPERATION THEREOF

(71) Applicant: REWALK ROBOTICS LTD., Yokneaam (IL)

(72) Inventor: Ofir Koren, Kadima (IL)

(73) Assignee: REWALK ROBOTICS LTD., Yokneam (IL)

( * ) Notice: Subject to any disclaimer, the term of this patent is extended or adjusted under 35 U.S.C. 154(b) by 750 days.

(21) Appl. No.: 14/631,897

(22) Filed: Feb. 26, 2015

(65) Prior Publication Data

US 2016/0250093 A1    Sep. 1, 2016

(51) Int. Cl.
| | |
|---|---|
| *A61H 3/00* | (2006.01) |
| *A61F 2/60* | (2006.01) |
| *A61F 5/02* | (2006.01) |
| *A61H 1/02* | (2006.01) |

(52) U.S. Cl.
CPC ............. *A61H 3/00* (2013.01); *A61F 2/60* (2013.01); *A61F 5/02* (2013.01); *A61H 1/024* (2013.01); *A61H 1/0244* (2013.01); *A61H 2201/0192* (2013.01); *A61H 2201/1633* (2013.01); *A61H 2201/5069* (2013.01)

(58) Field of Classification Search
CPC ........ A61H 1/02; A61H 1/0237; A61H 1/024; A61H 1/0244; A61H 1/0255; A61H 1/0262; A61H 2001/0211; A61H 3/00; A61H 2003/007; A61H 2201/0107; A61H 2201/0157; A61H 2201/0173; A61H 2201/0192; A61H 2201/1633; A61H 2201/5069; A61H 2201/0176; A61H 2201/1628; A61H 2201/164; A61H 2201/1642; A61H 2203/0406; A61H 2203/0418; A61H 2203/0431; A61H 2205/088; A61H 2205/10; A61H 2205/106; A61H 2205/108; A61F 5/02; A61F 2/60

See application file for complete search history.

(56) References Cited

U.S. PATENT DOCUMENTS

| | | | | |
|---|---|---|---|---|
| 406,328 | A | * | 7/1889 | Yagn ..................... A63B 25/10 297/4 |
| 2,010,482 | A | * | 8/1935 | Cobb .................... A61F 5/0102 446/377 |
| 4,253,479 | A | * | 3/1981 | Laurent .................. A45B 3/00 135/69 |

(Continued)

OTHER PUBLICATIONS

International Search Report and Written Opinion, dated May 3, 2016 for International Application No. PCT/US2016/019963, filed Feb. 26, 2016.

*Primary Examiner* — Steven Douglas
(74) *Attorney, Agent, or Firm* — Cooley LLP

(57) ABSTRACT

An exoskeleton device includes a plurality of braces that are each attachable to a part of a user. A plurality of joints connects adjacent braces. Each joint is controllable to bend or unbend so as to cause the exoskeleton device to change between an erect configuration and a sitting configuration. At least one support column is extendible from a brace. A length of the support column is adjustable. A controller is configured to adjust the length of the support column in coordination with the bending or unbending of a joint to provide support for the exoskeleton device when in the sitting configuration.

22 Claims, 7 Drawing Sheets

(56) References Cited

U.S. PATENT DOCUMENTS

| | | | |
|---|---|---|---|
| 4,456,086 A | 6/1984 | Weir et al. | |
| 5,020,790 A * | 6/1991 | Beard | A61F 5/0102 482/4 |
| 5,282,460 A * | 2/1994 | Boldt | A61F 2/68 403/119 |
| 5,476,441 A * | 12/1995 | Durfee | A61F 5/0102 434/112 |
| 7,628,766 B1 * | 12/2009 | Kazerooni | A61F 5/00 601/35 |
| 7,662,048 B2 * | 2/2010 | Libby | A63B 69/3608 473/207 |
| 9,610,208 B2 * | 4/2017 | Kazerooni | B25J 9/0006 |
| 9,687,408 B2 * | 6/2017 | Nagasaka | A61H 3/00 |
| 2007/0233279 A1 * | 10/2007 | Kazerooni | A61F 2/68 623/24 |
| 2008/0249438 A1 * | 10/2008 | Agrawal | A61H 1/0237 601/35 |
| 2010/0094188 A1 | 5/2010 | Goffer et al. | |
| 2011/0166489 A1 * | 7/2011 | Angold | A61H 1/0255 601/34 |
| 2011/0266323 A1 | 11/2011 | Kazerooni et al. | |
| 2013/0226048 A1 * | 8/2013 | Unluhisarcikli | A61H 3/00 601/34 |
| 2015/0018737 A1 * | 1/2015 | Threlfall | A61H 3/02 602/20 |

\* cited by examiner

EXOSKELETON DEVICE WITH SITTING SUPPORT AND METHOD OF OPERATION THEREOF

FIELD OF THE INVENTION

The present invention relates to exoskeletons. More particularly, the present invention relates to an exoskeleton device with a sitting support and a method of operation thereof.

BACKGROUND OF THE INVENTION

About 6 million people in the developed countries of the world are confined to wheelchairs due to lower limb disabilities. Such lower limb disabilities may be caused by injury such as spinal cord injury or traumatic brain injury, or by such diseases as stroke, cerebral palsy, spinal bifida, multiple sclerosis, or by other types of injuries or diseases. Confinement to a wheelchair may cause severe physiological and psychological deterioration, and may lead to poor health or quality of life, or low self-esteem. As a result, confinement to a wheelchair may lead to high medical expenses. Wheelchair users strive for assistive devices that would enable upright mobility, and thus improve their health, quality of life, and position in society.

Exoskeleton devices that attach to the body of a disabled person and enable the person to walk have been described. Such an exoskeleton device may be controlled to perform a variety of movements. Such an exoskeleton device may be operated to enable the person to walk without the assistance of others, and while standing or while leaning on crutches. Exoskeleton devices may be controlled to enable activities and access to places that may be difficult or impossible using a wheelchair.

SUMMARY OF THE INVENTION

There is thus provided, in accordance with an embodiment of the present invention, an exoskeleton device including: a plurality of braces that are each attachable to a part of a user; a plurality of joints that connect adjacent braces of the plurality of braces, each joint being controllable to bend or unbend so as to cause the exoskeleton device to change between an erect configuration and a sitting configuration; at least one support column that is extendible from a brace of the plurality of braces, a length of the at least one support column being adjustable; and a controller configured to adjust the length of the at least one support column in coordination with the bending or unbending of a joint of the plurality of joints to provide support for the exoskeleton device when in the sitting configuration.

Furthermore, in accordance with an embodiment of the present invention, the controller is further configured to adjust the length of the at least one support column in coordination with the bending or unbending of the joint to provide support for the exoskeleton device when changing between the erect configuration and the sitting configuration.

Furthermore, in accordance with an embodiment of the present invention, the controller is configured to extend the at least one support column to a supporting surface at the beginning of a sitting operation, and to shorten the at least one support column as the sitting operation progresses.

Furthermore, in accordance with an embodiment of the present invention, the brace of the plurality of braces is a torso brace.

Furthermore, in accordance with an embodiment of the present invention, the at least one support column includes a plurality of telescoping segments.

Furthermore, in accordance with an embodiment of the present invention, the controller is configured to adjust an angle of the at least one support column.

Furthermore, in accordance with an embodiment of the present invention, the controller is configured to gradually extend the at least one support column as a sitting operation progresses.

Furthermore, in accordance with an embodiment of the present invention, the at least one support column includes two support columns.

Furthermore, in accordance with an embodiment of the present invention, the controller is configured to extend the at least one support column to maintain contact with a supporting surface during the course of a standing operation.

Furthermore, in accordance with an embodiment of the present invention, the controller is configured to retract the at least one support column at the end of the standing operation.

Furthermore, in accordance with an embodiment of the present invention, the controller is configured to gradually shorten the at least one support column during the course of a standing operation.

There is further provided, in accordance with an embodiment of the present invention, a method of controlling a sitting operation of an exoskeleton device, the device including braces that are each attachable to a part of a user and a plurality of joints such that each joint connects adjacent braces of the braces, and at least one support column having an adjustable length, the method including: extending the at least one support column; bending the joints to a sitting configuration; and adjusting the length of the at least one support column in coordination with the bending of the joints.

Furthermore, in accordance with an embodiment of the present invention, adjusting the length includes extending the at least one support column to a support surface.

Furthermore, in accordance with an embodiment of the present invention, adjusting the length includes shortening the at least one support column in coordination with the bending.

Furthermore, in accordance with an embodiment of the present invention, adjusting the length includes gradually extending the at least one support column in coordination with the bending.

Furthermore, in accordance with an embodiment of the present invention, the method further includes adjusting an angle of the at least one support column.

There is further provided, in accordance with an embodiment of the present invention, a method of controlling a standing operation of an exoskeleton device, the device including braces that are each attachable to a part of a user and a plurality of joints such that each joint connects adjacent braces of the braces, and at least one support column having an adjustable length, the method including: unbending the joints to a standing configuration; and adjusting the length of the at least one support column in coordination with the unbending of the joints.

Furthermore, in accordance with an embodiment of the present invention, adjusting the length includes lengthening the at least one support column in coordination with the unbending to maintain contact of the at least one support column with a support surface.

Furthermore, in accordance with an embodiment of the present invention, the method further includes retracting the at least one support column when the standing configuration is attained.

Furthermore, in accordance with an embodiment of the present invention, adjusting the length includes shortening the at least one support column in coordination with the unbending.

BRIEF DESCRIPTION OF THE DRAWINGS

In order for the present invention, to be better understood and for its practical applications to be appreciated, the following figures are provided and referenced hereafter. It should be noted that the Figures are given as examples only and in no way limit the scope of the invention. Like components are denoted by like reference numerals.

DETAILED DESCRIPTION OF THE INVENTION

Figure 1A:
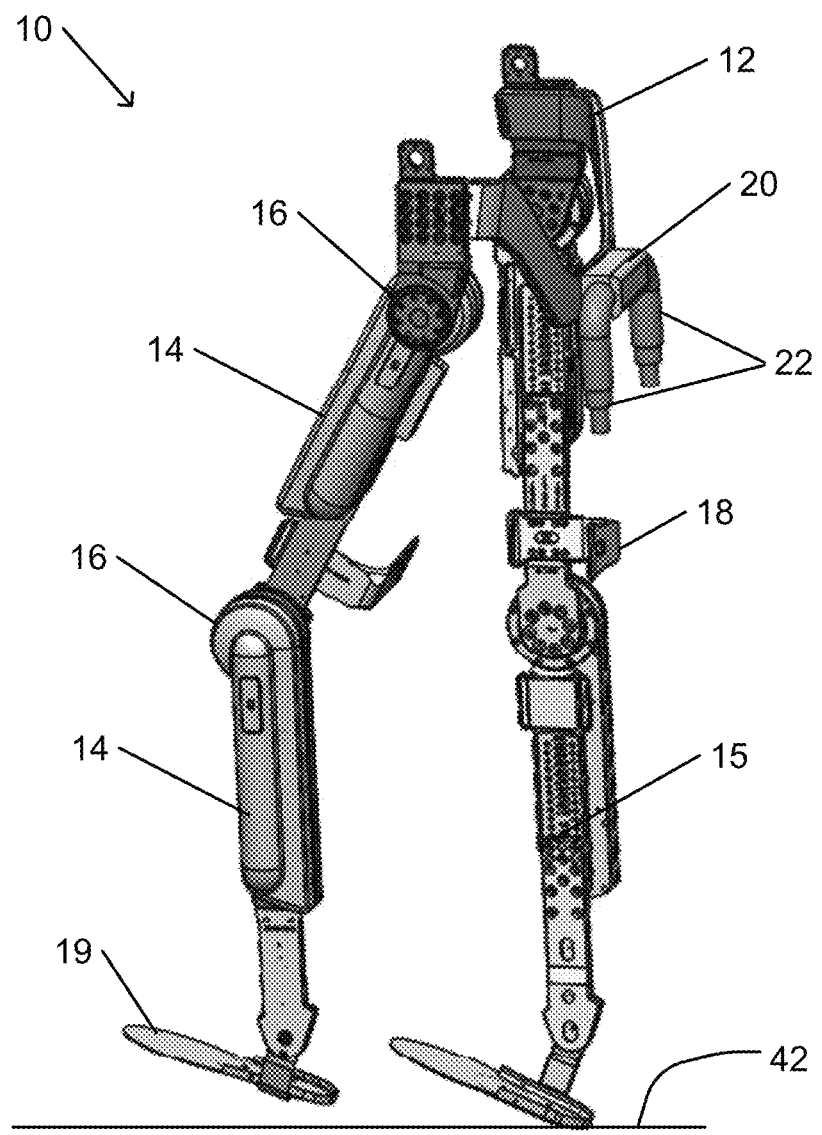
FIG. 1A schematically illustrates an exoskeleton device with an integrated sitting support in a standing configuration, in accordance with an embodiment of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, units, elements, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, us of the conjunction "or" as used herein is to be understood as inclusive (any or all of the stated options).

In accordance with an embodiment of the present invention, an exoskeleton device is configured to enable a user to sit. The user may typically be a person whose lower limbs are disabled, and who uses the exoskeleton device to assist in walking or other maneuvers.

The exoskeleton device may be attached to the user's body. For example, various braces of the exoskeleton device may be strapped, clamped, or otherwise attached to corresponding parts of the user's body. Such braces may typically include a pelvic or torso brace that attaches to the user's pelvis or lower torso, and various leg braces that attach to segments (e.g., thigh, lower leg, or foot) of the user's legs.

The each brace may be joined or connected to one or more adjacent braces via a motorized or otherwise actuated joint. Typically, the joints in the exoskeleton braces, when attached to the user, are located adjacent to corresponding joints (e.g., hip, knee, or ankle) of the user. One or more of the joints may be operated via a controller to bend, thus bending the corresponding joints of the user. The joints may be operated in a predetermined sequence, and subject to predetermined conditions, move with a walking gait or to perform another action. For example, the user may operate a control, perform one or more manipulations (e.g., lean forward or in another direction, exert a leaning force on a leg or foot brace, tilt the torso brace, or another manipulation), or both in order to initiate an action or to continue an action. The joints may be controlled to bend or unbend to cause the exoskeleton to change between an erect configuration and a sitting configuration.

For example, the user may operate a control to indicate an intention or desire to sit. Joints of the exoskeleton device, such as knee and hip joints, may be actuated to bend or flex to bring the user to a sitting position. Concurrently, an extender mechanism may be operated to extend (e.g., telescope outward, unfurl, or otherwise extend) one or more support columns downward toward the ground, floor, or other surface that is directly beneath the exoskeleton device and upon which the user or the exoskeleton device is support. Such a surface is herein referred to as a support surface. Typically, the extension is concurrently downward and rearward, at an oblique angle to the vertical. For example, the oblique angle may be in the range of about 10° to about 45°. The angle to the vertical may change (e.g., gradually decrease) during the course of a sitting operation.

The support columns may be extendible downward from one or more of the braces. For example, one or more of the support columns may be extendible from a torso brace, from a thigh brace, or elsewhere on the exoskeleton device. In some cases, the support columns may be extendible from an upper portion (when attached to a user in an upright standing position) of the exoskeleton device.

The concurrent bending of the joints and the extension of the support columns may bring the user to a stable sitting position. In the stable sitting position, the center of gravity of the user and exoskeleton device may be stably positioned between the legs of the user, as attached to leg braces of the exoskeleton device, and the extended support columns. The user's body may be supported while seated by various restraining structure (e.g., straps, bars, pads, trays, or other structure) that is incorporated into a part of the exoskeleton device that supports the user's thighs, hips, pelvis, or buttocks).

For example, the extender mechanism may rapidly extend the support columns to contact the support surface at the beginning of the sitting operation. During the continuation of the sitting operation, as the joints continue to bend, the extender mechanism may be operated to gradually shorten the support columns as the sitting operation progresses until the final sitting position is attained.

When the user operates a control to indicate an intention to stand from the sitting position, the joints of the exoskeleton device may be actuated to straighten or unbend. Concurrently, the extender mechanism may be operated to retract the columns (e.g., to telescope inward, fold, or otherwise retract). The angle of the columns to the vertical may change (e.g., gradually increase) during the course of a standing operation.

In some cases, prior to retracting the columns, the extender mechanism may be operated to initially further extend the columns to remain in contact with the support surface during the standing procedure. When the standing operation is concluded, or is close to being concluded (e.g., a bending angle of one or more of the joints is less than a threshold value), the support columns may be retracted.

An exoskeleton device with an integrated sitting support may be advantageous over other devices that enable mobility and a sitting capability. A user of an exoskeleton device may require rest when a suitable seat is not available. For example, the user may be in an open area where no a person in an exoskeleton without an integrated may not always be able to find a suitable chair or surface on which to sit. For example, an armchair may be too narrow to accommodate the exoskeleton device. A backless bench or chair may not provide sufficient stability. A mobile chair with a standing capability may not be able to access places that would be accessible to a person in an exoskeleton device.

The support columns may also serve a function during use other than sitting or standing. For example, during a walking or ambulation operation, the support columns may remain partially extended. Thus, the support columns may provide an additional safety measure to prevent falling backward.

Figure 1B:
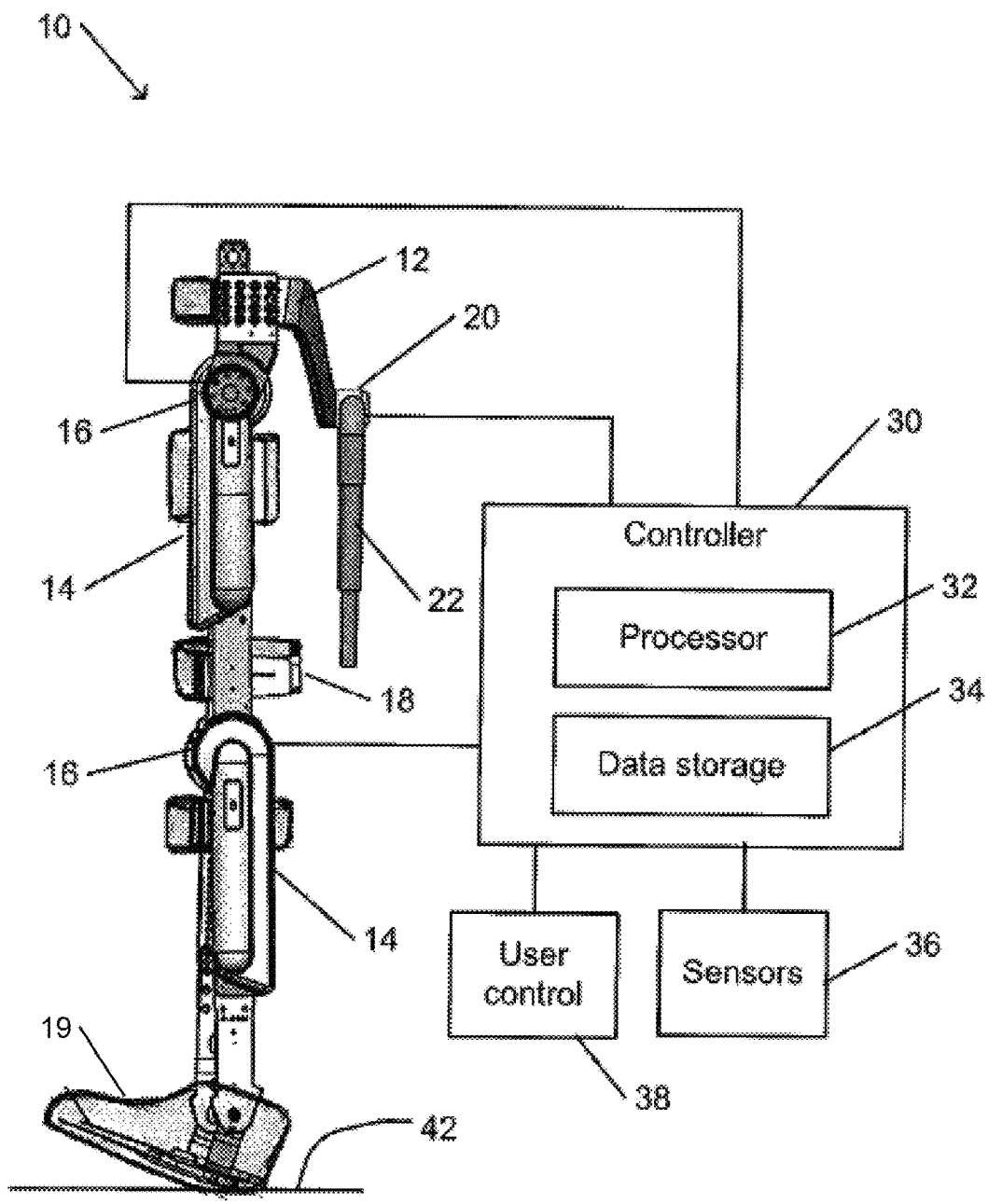
FIG. 1B schematically illustrates components related to control of the exoskeleton device shown in FIG. 1A.

FIG. 1A schematically illustrates an exoskeleton device with an integrated sitting support in a standing configuration, in accordance with an embodiment of the present invention. FIG. 1B schematically illustrates components related to control of the exoskeleton device shown in FIG. 1A.

Exoskeleton device 10 includes torso brace 12. Torso brace 12 may be attached using one or more straps, bands, belts, clamps, or other structure to a pelvis or lower torso of a user. Each leg brace 14 may be similarly attached to a part of the user's leg (thigh or lower leg). Leg braces 14 may include adjustment structure 15 to fit a leg brace 14 to a part of the user's leg to which that leg brace 14 is to attach. Leg supports 18 may be configured to attach to, hold, support, or lift a part (e.g., thigh, leg, or other part) of the user's leg. For example, a leg support 18 may include brackets, straps, or other structure to attach to or support a part of the leg. A foot support 19 may be configured to attach to hold, support, or lift a foot of the user. For example, foot support 19 may include a shoe upper, brackets, straps or other structure to attach to, hold, or support a foot. A buttocks support 17 (FIG. 2), e.g., including brackets, straps, or other structure may be configured to support the user's buttocks and torso when exoskeleton device 10 is in a sitting configuration.

Adjacent braces (e.g., torso brace 12 and leg braces 14) of exoskeleton device 10 are joined to one another via a controllable joints 16. Each controllable joint 16 is motorized or otherwise provided with an actuator. The actuator may be controlled to adjust a controllable joint 16 to change a relative orientation of the two braces that are joined by that controllable joint 16. For example, controllable joint 16 may include a rotary motor and a suitable rotary transmission. Controllable joint 16 may include an encoder or other sensor that may measure a current angle opening between the joined braces, a change in angle, or another indication of a current relative orientation, or change in relative orientation, of the joined braces.

Column extension mechanism 20 may be operated to extend or retract one or more support columns 22. Support columns 22 are extendible downward and rearward (e.g., to the rear of a user to whom exoskeleton device 10 is attached) of exoskeleton device 10. In the example shown, support columns 22 are extendible from torso brace 12. For example, column extension mechanism 20 may include, or communicate with, one or more mechanical, hydraulic, pneumatic, or electromagnetic actuators to extend or retract a support column 22. For example, support column 22 may include a plurality of telescoping or foldable sections. A length of support column 22 may be adjusted to a length in a range from a minimum length when support column 22 is fully retracted, to a maximum length when support column 22 is fully extended. For example, the maximum length may be sufficiently long such that support column 22 may reach support surface 42 when exoskeleton device 10 is erect (e.g., when all controllable joints 16 are unbent). The maximum length may be longer than a vertical distance from column extension mechanism 20 to the bottom of exoskeleton device 10 (e.g., the bottom of foot support 19). Thus, support column 22 may also reach support surface 42 when exoskeleton device 10 is erect and support surface 42 has an uphill slope (e.g., slopes upward ahead of the user).

Operation of one or more components of exoskeleton device 10 may be controlled by controller 30. Controller 30 may be incorporated into, mounted on, or may communicate with exoskeleton device 10. For example, one or more components of controller 30 may be mounted on or within one or more of torso brace 12, leg braces 14, column extension mechanism 20, controllable joints 16 or elsewhere on exoskeleton device 10. One or more components of controller 30 may be mounted or held in a backpack or other container that is worn or carried by the user of exoskeleton device 10, that is mounted to exoskeleton device 10, or that is remote from exoskeleton device 10 (e.g., communicating via a wired or wireless connection). One or more components of controller 30 may be housed together with, or adjacent to, a battery or other power source for operation of exoskeleton device 10.

Controller 30 may control operation of one or more of controllable joints 16 and column extension mechanism 20. Controller 30 may operate in response to a signal received from user control 38 or a sensor 36.

User control 38 may include one or more user operable controls that may be operated by a user of exoskeleton device 10 or by another operator (e.g., a technician or other maintenance or training personnel, a person offering assistance to or taking care of the user, or other person). The controls may include one or more devices that may be manipulated or otherwise operated to indicate a command to perform or halt an operation or action. Such devices may include, for example, pushbuttons or keys, levers, dials, knobs, pointing devices, touch sensitive devices (e.g., buttons, pads, screens, or other touch sensitive devices), microphones or other sound sensitive devices, or other user-operable devices. One or more devices of user control 38 may be located on controller 30, exoskeleton device 10, or on a remote control unit that is accessible to a user or operator of exoskeleton device 10. Operation of a user control 38 may generate a signal that is transmitted to, and interpretable by, controller 30.

Sensors 36 may include one or more sensing devices that are configured to generate a signal that is indicative of a sensed quantity. The signal may be transmitted to, and interpreted by, controller 30. Some or all of sensors 36 may be located on exoskeleton device 10 or on the user (e.g., worn or attached to the user). For example, sensors 36 may include one or more angle sensors (e.g., encoders or other angle sensors) to sense a bending angle of a controllable joint 16 (e.g., to monitor operation of controllable joints 16) or of another joint (e.g., a non-motorized joint such as between a foot support 19 and an adjacent leg brace 14). Sensors 36 may include one or more tilt sensors to sense a tilt of exoskeleton device 10 (e.g., of torso brace 12 or a leg brace 14), or of the user (e.g., worn on the torso or elsewhere on the user). A tilt sensor reading may be interpreted to detect falling, to initiate an action or determine that an action is enabled (e.g., a step of a walking gait or other action), or to monitor progress of an action. Sensors 36 may include one or more inertial sensors (e.g., accelerometers, gyroscopes, or other inertial sensors) that sense a change in orientation or acceleration of exoskeleton device 10 or of the user (e.g., to detect falling or other condition requiring attention). Sensors 36 may include one or more ground force sensors that detect a force exerted by a part of exoskeleton device 10 (e.g., foot support 19, support column 22, or another component of exoskeleton device 10) on support surface 42 (e.g., to monitor progress of an action, to detect leaning on a leg brace, to detect falling, or other condition requiring attention). Sensors 36 may include one or more proximity sensors to sense a distance from a surface or object, or contact sensors to detect contact of a component of exoskeleton device 10 (e.g., a support column 22) with a surface or object.

Controller 30 may include processor 32. Processor 32 may include one or more intercommunicating processing units, which may be remote from one another (e.g., housed separately on or within exoskeleton device 10 or elsewhere). Processor 32 may be configured to operate in accordance with programmed instructions, e.g., as stored in data storage unit 34.

Data storage unit 34 may include one or more fixed or removable, volatile or nonvolatile, data storage or memory devices. Data storage unit 34 may be utilized to store, for example, programmed instructions for operation of processor 32, data or parameters for use by processor 32 during operation, or results of operation of processor 32.

For example, when instructed by operation of user control 38, controller 30 may operate exoskeleton device 10 to begin a sitting operation. A sitting operation includes operating controllable joints 16 to bend to bring the user to a sitting position. During the sitting operation, support columns 22 are extended. Thus, the center of gravity of the user and exoskeleton device 10 are stably supported between extended support columns 22 and foot supports 19 when exoskeleton device 10 is in a sitting or partially seated configuration.

Figure 2:
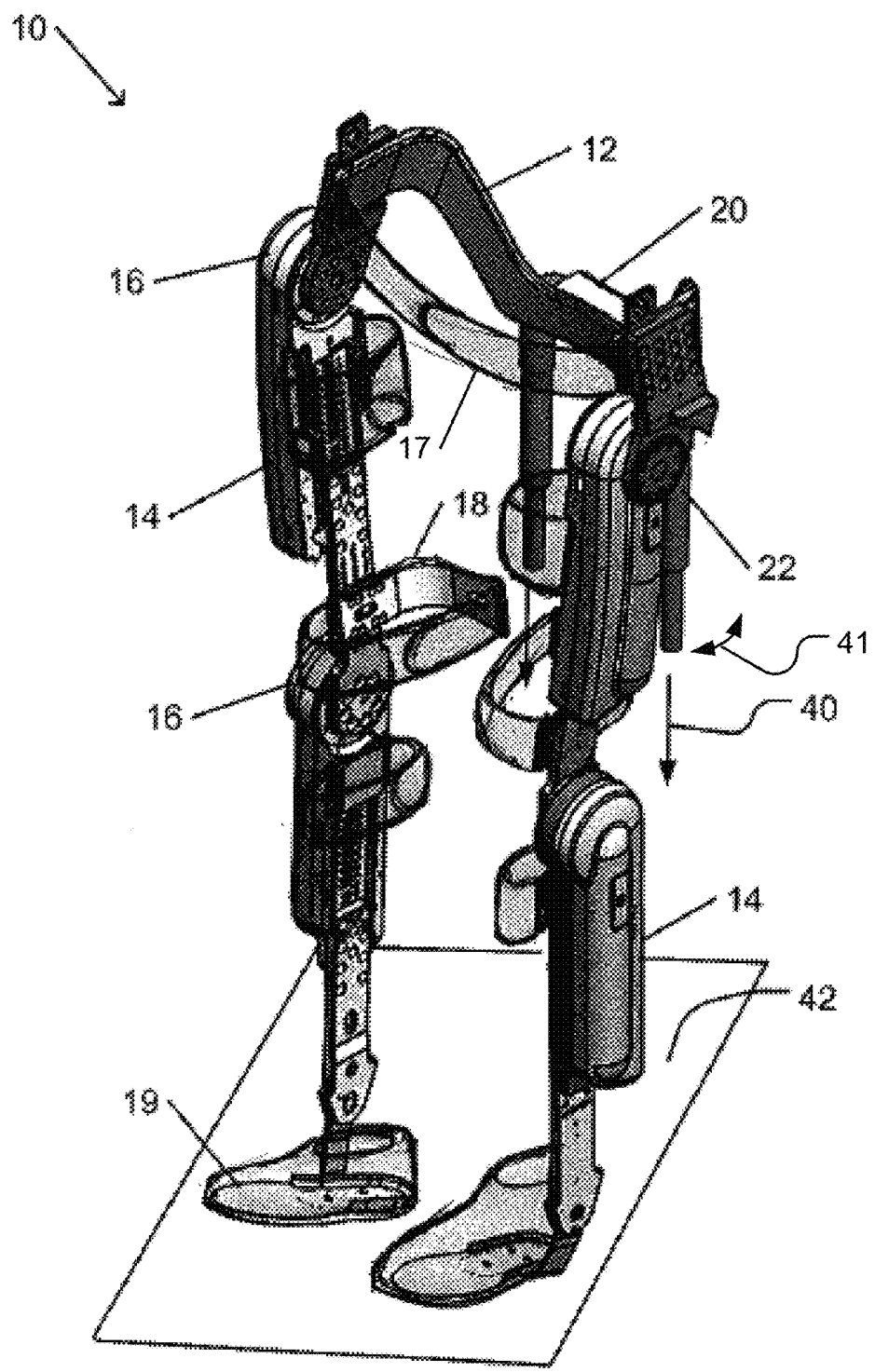
FIG. 2 schematically illustrates the exoskeleton device shown in FIG. 1A in an erect configuration at the beginning of a sitting operation.

FIG. 2 schematically illustrates the exoskeleton device shown in FIG. 1A in an erect configuration at the beginning of a sitting operation.

When a sitting operation is initiated, exoskeleton device 10 may be in an erect configuration such that the user to whom exoskeleton device 10 is standing erect. For example, all controllable joints 16 may be in unbent configurations. In some cases, a sitting operation may be initiated from another configuration (e.g., leaning, crouching, bowing, walking, partially sitting, or another configuration).

When beginning the sitting operation, or at a time after beginning a sitting operation, column extension mechanism 20 may be operated to extend one or more support columns 22 with extension motion 40. Support columns 22 may be initially extended to contact or approach (e.g., to within a predetermined distance of) support surface 42. For example, support columns 22 may be extended downward and rearward to a predetermined length that had been previously determined to reach support surface 42. Alternatively or in addition, the contact or approach (e.g., within a predetermined distance) of a distal end of support column 22 to support surface 42 may be determined by a contact or proximity sensor. Thus, when support surface 42 is uneven (e.g., sloped, rocky, includes hills or pits, or includes other objects or topography), different support columns 22 may be extended to different lengths.

Column extension mechanism 20 may also be configured to control or change an angle of a support column 22 relative to the vertical with tilt motion 41. For example, during a sitting operation, an angle of support column 22 may change from an initial angle (e.g., sloping downward and rearward from column extension mechanism 20 to support surface 42) to a final angle (e.g., closer to vertical on a level support surface 42).

As another example, support columns 22 may be extended gradually as one or more controllable joints 16 are bent so as to provide support when it is required (e.g., when a center of gravity of the user and exoskeleton device 10 moves laterally to the position of foot supports 19 such that additional support is required). The user may manipulate crutches to provide support during the gradual extension of support columns 22.

For example, column extension mechanism 20 may operate a motorized or otherwise operated actuator that extends telescoping segments of a support column 22. One or more compressed mechanical, hydraulic, or pneumatic springs may be released to extend telescoping segments of support column 22. Threaded telescoping segments of support column 22 may be rotated to extend the telescoping segments. Another mechanical mechanism (e.g., a system of pulleys and tension wires, thermal expansion, A pump may operate a hydraulic or pneumatic mechanism to extend telescoping segments of support column 22. Electromagnetic repulsion or another mechanism may be applied to extend telescoping segments of support column 22.

Telescoping segments of support column 22 may be provided with one or more catches, locks, or brakes, or another fixing mechanism. The fixing mechanism may be continuous (e.g., by operation of a brake or clamp), such that support column 22 may be fixed at any length (e.g., minimum, intermediate, or maximum). In some cases, the fixing mechanism may be configured (e.g., by spaced catches or locks) to fix the length of support column 22 at one or more predetermined stop positions or discrete lengths of support column 22. A fixing mechanism may be configured to automatically activate in the event of a power failure, or other predetermined malfunction or failure condition.

Alternatively or in addition to telescoping segments, one or more other mechanisms may be provided to extend support column 22. For example, support column 22 may include inflatable structure (e.g., with accordion pleating, or otherwise), folded or coiled structure that may be opened, unfolded, unfurled, or uncoiled, thermally or otherwise activated memory materials, or another mechanism for extending support column 22.

Before, after, or concurrently with extension of support columns 22, controllable joints 16 may be operated to begin to bend. The bending of controllable joints 16 may bring exoskeleton device 10 from an erect or standing configuration toward a sitting configuration.

Throughout the sitting operation, the user may manipulate crutches, or otherwise act (e.g., by grasping nearby structure), to assist in maintaining stability throughout the sitting operation.

Figure 3:
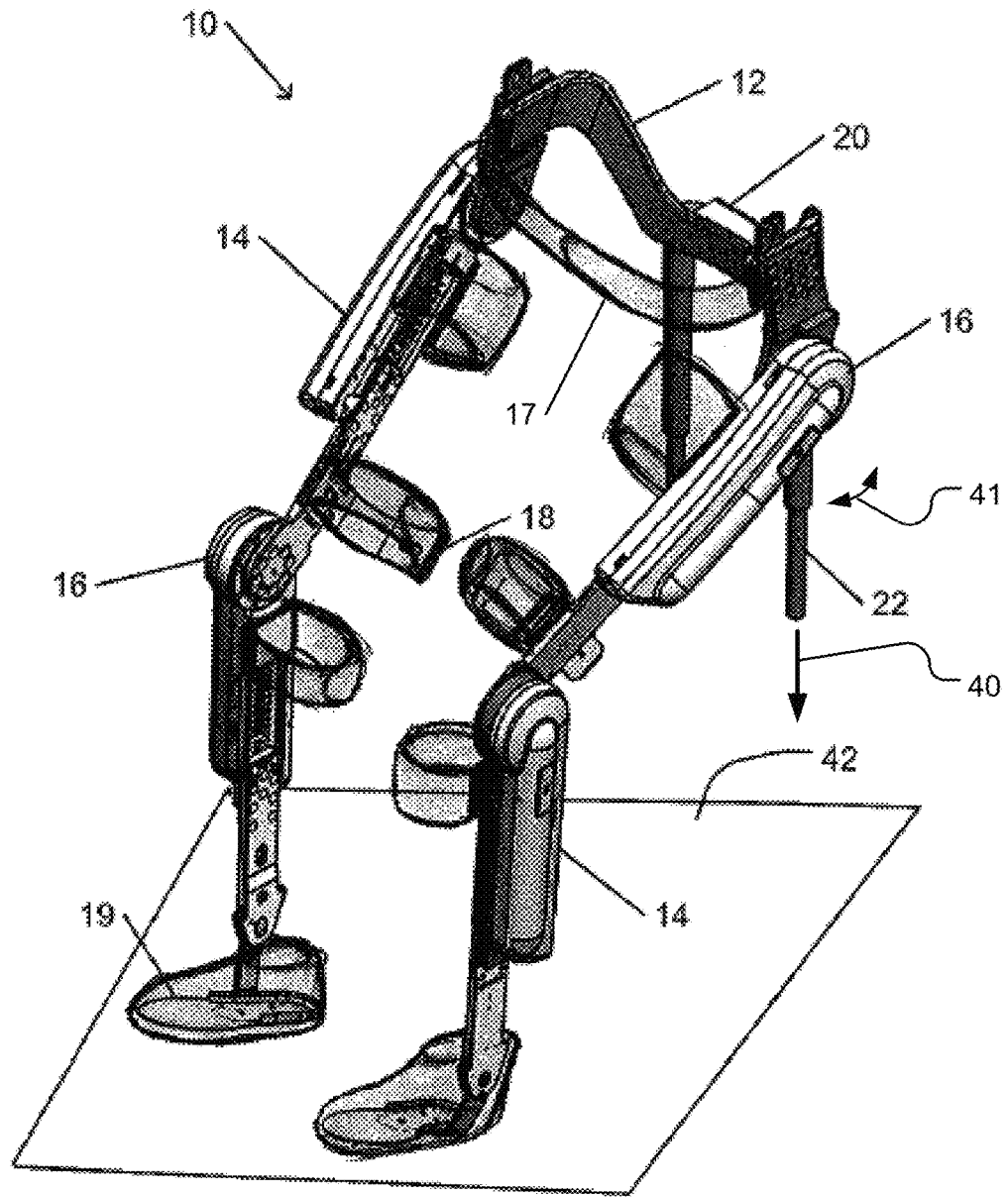
FIG. 3 schematically illustrates the exoskeleton device shown in FIG. 1A in a partially seated configuration during a sitting operation.

FIG. 3 schematically illustrates the exoskeleton device shown in FIG. 1A in a partially seated configuration during a sitting operation.

As shown, controllable joints 16 have been controlled to bend to an oblique angle between 0° (erect or standing) and 90° (sitting). Support columns 22, which may have initially extended to support surface 42 when exoskeleton device 10 was in an erect configuration, have been shortened together with the bending of controllable joints 16. For example, column extension mechanism 20 may have been operated to partially retract support columns 22, e.g., by operating an extension mechanism in reverse. By maintaining contact of support columns 22 with support surface 42, exoskeleton device 10 may remain stable throughout the sitting operation. Therefore, in the event that the sitting operation is interrupted (e.g., by a power failure, or other malfunction or predetermined condition), the user may continue to be stably supported by exoskeleton device 10.

The sitting operation of concurrently bending controllable joints 16 and adjusting the length of support columns 22 may continue until exoskeleton device 10 is in a sitting configuration.

Figure 4A:
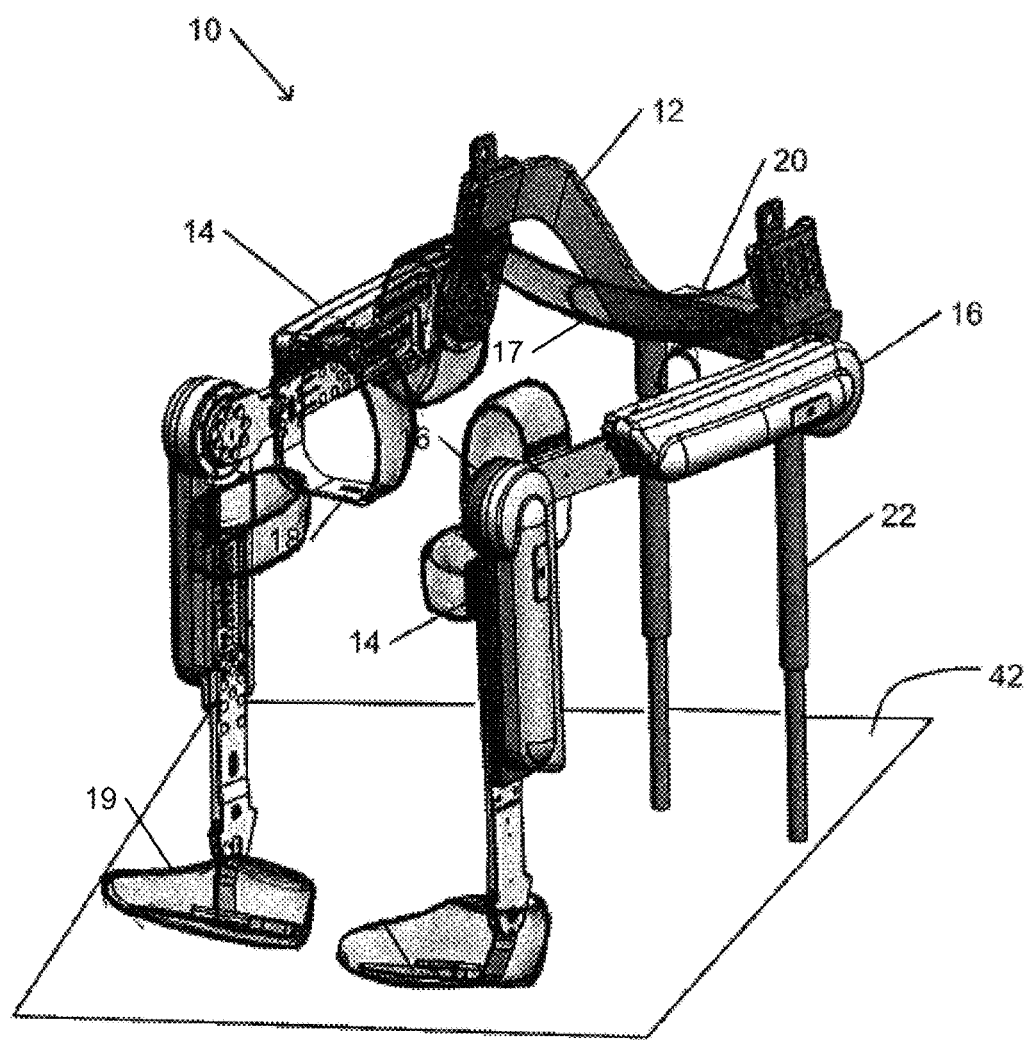
FIG. 4A schematically illustrates the exoskeleton device shown in FIG. 1A in a sitting configuration at the end of a sitting operation.
Figure 4B:
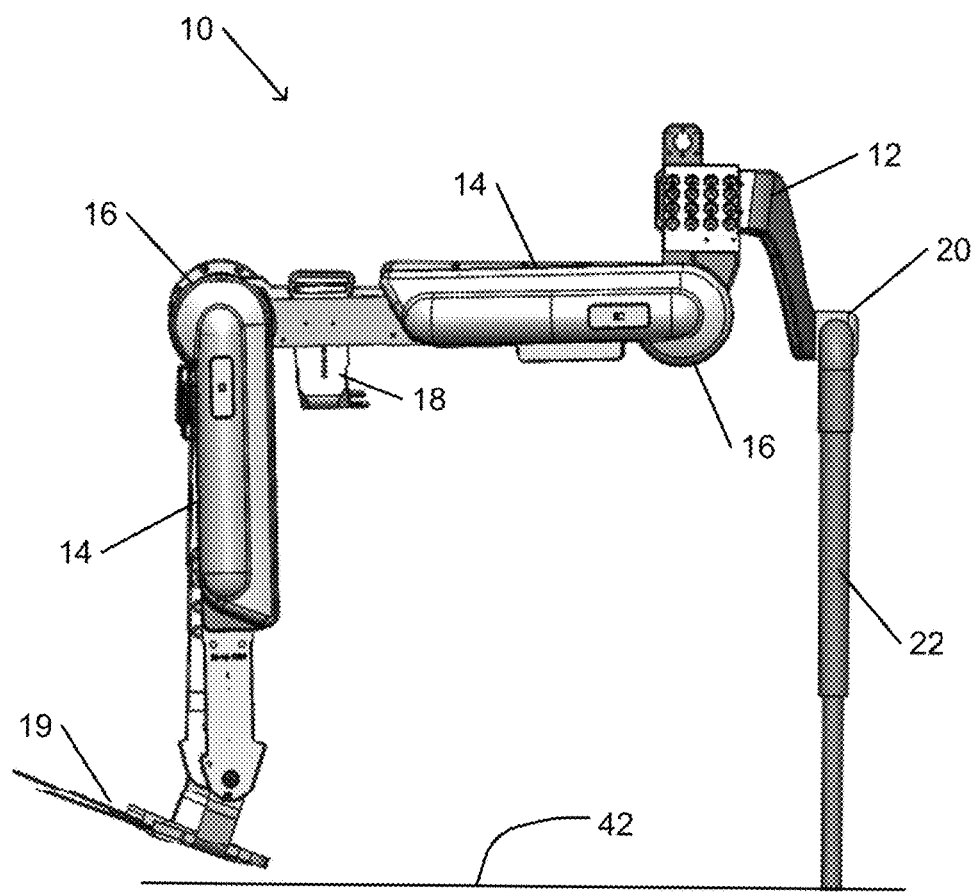
FIG. 4B is a schematic side view of the configuration shown in FIG. 4A.

FIG. 4A schematically illustrates the exoskeleton device shown in FIG. 1A in a sitting configuration at the end of a sitting operation. FIG. 4B is a schematic side view of the configuration shown in FIG. 4A.

When the sitting operation is complete, controllable joints 16 are bent approximately by about 90° (e.g., lower leg approximately perpendicular to thigh at knee, thigh approximately perpendicular to torso at hip). The lengths of one or more support columns 22 have been adjusted (e.g., partially retracted) to extend to support surface 42 when in the sitting configuration. The lengths of support columns 22 may have been fixed. The body of the user (e.g., one or more of the user's thigh, buttocks, and pelvic region) are supported by support structure 18.

When instructed by operation of an appropriate control or sensor, exoskeleton device 10 may be controlled to begin a standing operation. A standing operation includes operating controllable joints 16 to straighten or unbend to bring the user to a standing position. During the standing operation, support columns 22 are lengthened. Thus, the center of gravity of the user and exoskeleton device 10 remains stably supported between support columns 22 and foot supports 19 when exoskeleton device 10 is in a partially seated or standing configuration.

At the beginning of the standing operation, exoskeleton device 10 is in a sitting configuration, as shown in FIGS. 4A and 4B. Lengths of support columns 22 have been adjusted to contact support surface 42 in the sitting configuration.

To begin the standing operation, controllable joints 16 are operated to unbend by reducing their bending angles. Concurrently, support columns 22 may be lengthened to maintain contact with support surface 42 and to maintain stability of exoskeleton device 10. In a case were an extending force to lengthen a support column 22, the lengthening of support column 22 may assist in raising exoskeleton device 10 to a standing configuration.

As controllable joints 16 are straightened and support columns 22 are lengthened, exoskeleton device 10 is in a partially seated configuration, as shown in FIG. 3.

Alternatively or in addition, support columns 22 may be gradually shortened during the course of the standing operation. Stability of exoskeleton device 10 may be maintained during the course of the standing operation by manipulation of crutches by the user.

Continued extension of controllable joints 16 and lengthening of support columns 22 may result in exoskeleton device 10 assuming an erect configuration, as shown in FIG. 2. At this point, support columns 22 may be fully retracted.

Throughout the standing operation, the user may manipulate crutches, or otherwise act (e.g., by grasping nearby structure), to assist in maintaining stability throughout, or otherwise assist with, the standing operation. For example, the exoskeleton device 10 may be configured to begin the standing operation only after reduced ground force on support columns 22 is sensed.

A controller of exoskeleton device 10 may be configured to control operation of exoskeleton device 10 during a sitting operation.

Figure 5A:
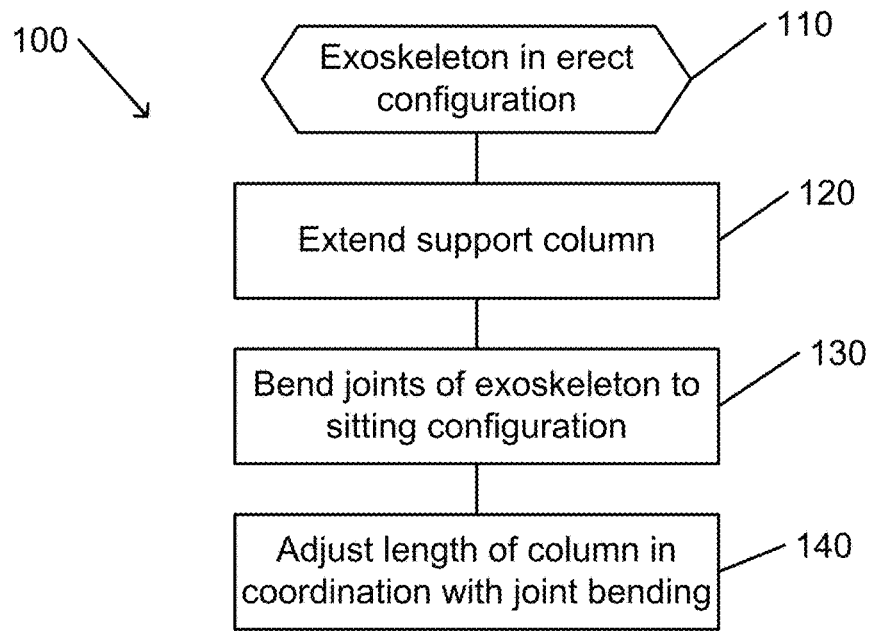
FIG. 5A is a flowchart depicting a sitting operation of an exoskeleton device with an integrated sitting support, in accordance with an embodiment of the present invention.

FIG. 5A is a flowchart depicting a sitting operation of an exoskeleton device with an integrated sitting support, in accordance with an embodiment of the present invention.

It should be understood with respect to any flowchart referenced herein that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of any flowchart referenced herein has been selected for convenience and clarity only. Operations of the illustrated method may be executed in an alternative order, or concurrently, with equivalent results. Such reordering of operations of the illustrated method should be understood as representing other embodiments of the illustrated method.

Sitting operation 100 may be executed by a controller of an exoskeleton device. Sitting operation 100 may be executed when the exoskeleton device is in an erect configuration (block 110).

The exoskeleton device may be operated to extend one or more support columns (block 120). For example, the support columns may be fully extended to reach a support surface, or may be partially extended.

Controllable joints of the exoskeleton device may be flexed or bent to bring the exoskeleton device to a sitting configuration (block 130). The lengths of the support columns may be adjusted, e.g., shortened or lengthened, in a manner that is coordinated with the bending of the joints (block 140). For example, the length of a support column may be adjusted in accordance with one or more sensor readings. An angle of the support column to the vertical may also be adjusted. The sensors readings may indicate, for example, a bending angle of a joint or a contact force between the support column and a support surface on which the exoskeleton device is place or located. The adjustment may be configured to provide stability to the exoskeleton device, to minimize stress on components of the exoskeleton device, to provide user comfort, or another purpose.

When the sitting operation is complete, the user may be in a sitting position.

A controller of an exoskeleton device may be configured to control operation of the exoskeleton device during a standing operation.

Figure 5B:
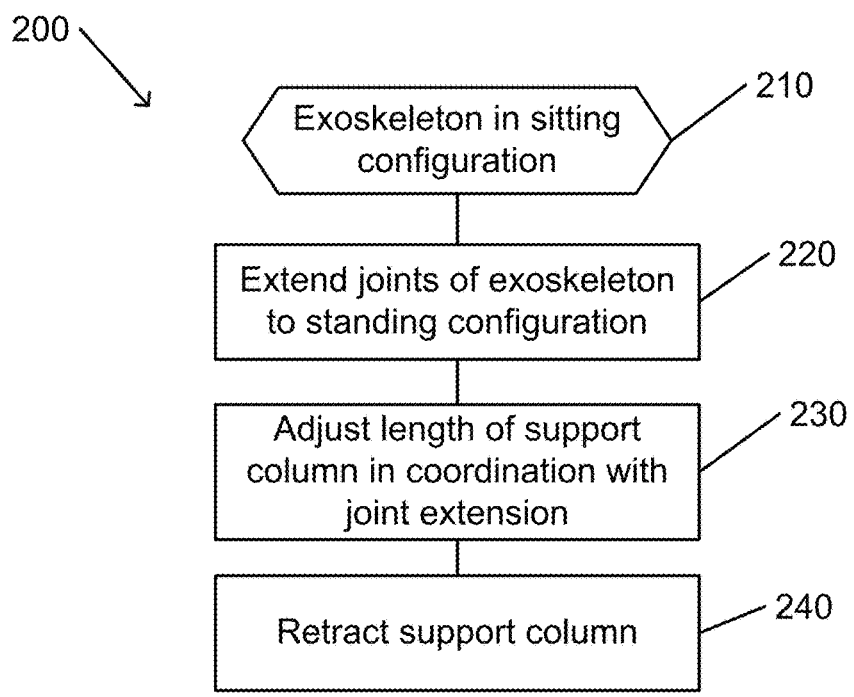
FIG. 5B is a flowchart depicting a standing operation of an exoskeleton device with an integrated sitting support, in accordance with an embodiment of the present invention.

FIG. 5B is a flowchart depicting a standing operation of an exoskeleton device with an integrated sitting support, in accordance with an embodiment of the present invention.

Standing operation 200 may be executed by a controller of an exoskeleton device. Standing operation 200 may be executed when the exoskeleton device is in a sitting configuration (block 210).

Controllable joints of the exoskeleton device may be straightened or unbent to bring the exoskeleton device to a standing configuration (block 220). The lengths of the support columns may be adjusted, e.g., lengthened or shortened, in a manner that is coordinated with the unbending of the joints (block 230). For example, the length of a support column may be adjusted in accordance with one or more sensor readings. An angle of the support column to the vertical may also be adjusted. The sensors readings may indicate, for example, a bending angle of a joint or a contact force between the support column and a support surface on which the exoskeleton device is place or located. The adjustment may be configured to provide stability to the exoskeleton device, to minimize stress on components of the exoskeleton device, to provide user comfort, or another purpose.

When the joints have been sufficiently straightened, e.g., when the exoskeleton device is in, or is sufficiently close to (e.g., bending angles are less than a threshold value) an erect configuration, the support columns may be fully or partially retracted (block 240). For example, retracting the support columns may prevent interference with another function of the exoskeleton device, such as walking or another function.

When the standing operation is complete, the user may be in a standing position.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An exoskeleton device comprising:
a plurality of braces that are each configured to be attached to a part of a user;
a plurality of joints that connect adjacent braces of said plurality of braces, each joint being controllable to bend or unbend so as to cause the exoskeleton device to change between an erect configuration and a sitting configuration;
at least one support column with an adjustable length having a first end configured to be attached to a brace of said plurality of braces, the at least one support column configured to be extendible from the first end such that a second end of the at least one support column directly contacts a support surface supporting the exoskeleton device during and/or at an end of a sitting operation of the exoskeleton device; and
a controller configured to adjust the length of said at least one support column in coordination with the bending or unbending of a joint of said plurality of joints to provide support for the exoskeleton device when in the sitting configuration.

2. The device of claim 1, wherein the controller is further configured to adjust the length of said at least one support column in coordination with the bending or unbending of the joint to provide support for the exoskeleton device when changing between the erect configuration and the sitting configuration.

3. The device of claim 2, wherein the controller is configured to extend said at least one support column to a supporting surface at the beginning of a sitting operation, and to shorten said at least one support column as the sitting operation progresses.

4. The device of claim 1, wherein said brace of said plurality of braces is a torso brace.

5. The device of claim 1, wherein said at least one support column comprises a plurality of telescoping segments.

6. The device of claim 1, wherein the controller is configured to adjust an angle of said at least one support column.

7. The device of claim 1, wherein the controller is configured to gradually extend said at least one support column as a sitting operation progresses.

8. The device of claim 1, wherein said at least one support column comprises two support columns.

9. The device of claim 1, wherein the controller is configured to extend said at least one support column to maintain contact with a supporting surface during the course of a standing operation.

10. The device of claim 9, wherein the controller is configured to retract said at least one support column at the end of the standing operation.

11. The device of claim 1, wherein the controller is configured to gradually shorten said at least one support column during the course of a standing operation.

12. The method of claim 1, wherein the brace of said plurality of braces includes a torso brace and the at least one support column is configured to be attached to the torso brace.

13. The method of claim 1, wherein the brace of said plurality of braces includes a thigh brace and the at least one support column is configured to be attached to the thigh brace.

14. A method of controlling a sitting operation of an exoskeleton device, the device including braces that are each configured to be attached to a part of a user and a plurality of joints such that each joint connects adjacent braces of the braces, and at least one support column having an adjustable length with a first end configured to be attached to a brace of the braces, the method comprising:
- extending said at least one support column from the first end such that a second end of the at least one support column directly contacts a support surface supporting the exoskeleton device during and/or at an end of a sitting operation of the exoskeleton device;
- bending the joints to a sitting configuration; and
- adjusting the length of said at least one support column in coordination with the bending of the joints.

15. The method of claim 14, wherein adjusting the length comprises extending said at least one support column to a support surface.

16. The method of claim 15, wherein adjusting the length comprises shortening said at least one support column in coordination with the bending.

17. The method of claim 14, wherein adjusting the length comprises gradually extending said at least one support column in coordination with the bending.

18. The method of claim 14, further comprising adjusting an angle of said at least one support column.

19. A method of controlling a standing operation of an exoskeleton device, the device including braces that are each configured to be attached to a part of a user and a plurality of joints such that each joint connects adjacent braces of the braces, and at least one support column: (1) having an adjustable length with a first end configured to be attached to a brace of the braces, and (2) configured to be extendible from the first end such that a second end of the at least one support column directly contacts a support surface supporting the exoskeleton device during and/or at an end of a sitting operation of the exoskeleton device, the method comprising:
- unbending the joints to a standing configuration; and
- adjusting the length of said at least one support column in coordination with the unbending of the joints.

20. The method of claim 19, wherein adjusting the length comprises lengthening said at least one support column in coordination with the unbending to maintain contact of said at least one support column with a support surface.

21. The method of claim 20, further comprising retracting said at least one support column when the standing configuration is attained.

22. The method of claim 19, wherein adjusting the length comprises shortening said at least one support column in coordination with the unbending.

* * * * *